Figure 1:
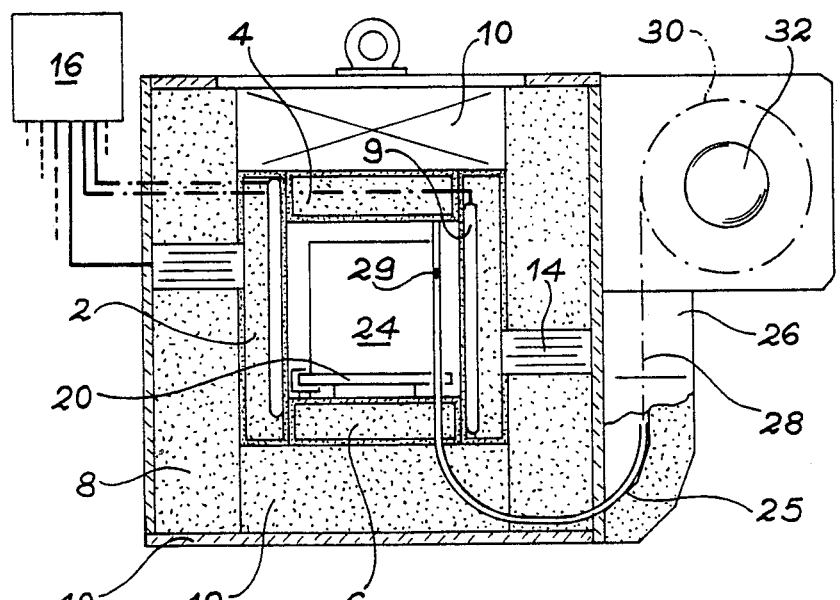

United States Patent [19]

Bernard et al.

[11] Patent Number: 4,897,550
[45] Date of Patent: Jan. 30, 1990

[54] APPARATUS FOR THE CHARACTERIZATION OF FISSILE MATERIAL HAVING AT LEAST ONE NEUTRON RADIATION DETECTOR LOCATED IN A GAMMA RADIATION DETECTION SCINTILLATOR

[75] Inventors: Patrice Bernard, Venelles; Jacques R. Dherbey, Aix en Provence; Roland Bosser, Pierrevert; Roger Berne, Aix en Provence, all of France

[73] Assignee: Commissariat a L'Energie Atomique, Paris, France

[21] Appl. No.: 234,177

[22] Filed: Aug. 19, 1988

[30] Foreign Application Priority Data

Aug. 21, 1987 [FR] France ................. 87 11805

[51] Int. Cl.⁴ .................. G01T 3/00; H01J 47/12; G21G 1/06
[52] U.S. Cl. .................. 250/390.01; 250/390.03; 250/390.11; 250/363.01; 376/154; 376/158; 376/159
[58] Field of Search ........ 250/390.01, 390.03, 250/390.11, 390.10, 390.04, 392, 393, 253, 518.1, 496.1, 497.1, 506, 361 R, 336.1, 363.01; 376/154, 158, 159

[56] References Cited

U.S. PATENT DOCUMENTS

| | | | |
|---|---|---|---|
| 3,272,987 | 9/1966 | Kohn et al. | 250/497.1 |
| 3,399,302 | 8/1968 | Carrell | 250/390.04 |
| 3,532,888 | 10/1970 | Masefield et al. | 250/497.1 |
| 3,564,255 | 2/1971 | Massey | 250/497.1 |
| 3,638,020 | 1/1972 | Duffey et al. | 250/253 |
| 3,736,429 | 5/1973 | Foley | 250/363.01 |
| 3,786,253 | 1/1974 | Haffner et al. | 250/390.1 |
| 3,786,256 | 1/1974 | Untermyer | 376/159 |
| 3,890,505 | 6/1975 | Olson | 250/361 |
| 4,225,790 | 9/1980 | Parsons, Jr. et al. | 250/497.1 |
| 4,266,132 | 5/1987 | Marshall | 250/359.1 |
| 4,393,307 | 7/1983 | Nozaki et al. | 250/390.01 |
| 4,658,142 | 4/1987 | Johnson et al. | 250/393 |

FOREIGN PATENT DOCUMENTS 0220099 4/1987 European Pat. Off. .

Primary Examiner—Janice A. Howell
Assistant Examiner—J. Eisenberg
Attorney, Agent, or Firm—Michael N. Meller

[57] ABSTRACT

It comprises an enclosure, a neutron emitting source (29) for bombarding said fissile material, means (28, 30) for introducing source (29) into the enclosure and for removing said source from the enclosure, neutron radiation detection means (9), moderator means (2, 4, 6) for thermalizing a fission radiation emitted by said fissile material interposed between the neutron radiation detection means (9) and the fissile material. It also has gamma radiation detection means (6, 14), which comprises a scintillator (6) and at least one photomultiplier (14) associated with said scintillator (6) and the scintillator material also constituting the moderator for thermalizing the fast neutrons directly emitted by the source (29), as well as the neutrons from the spontaneous fissions of the $\alpha$, n reaction and the neutrons from the fissions induced in the fissile material, the neutron radiation detectors (9) being embedded in the scintillator material (6) constituting the moderator.

8 Claims, 2 Drawing Sheets

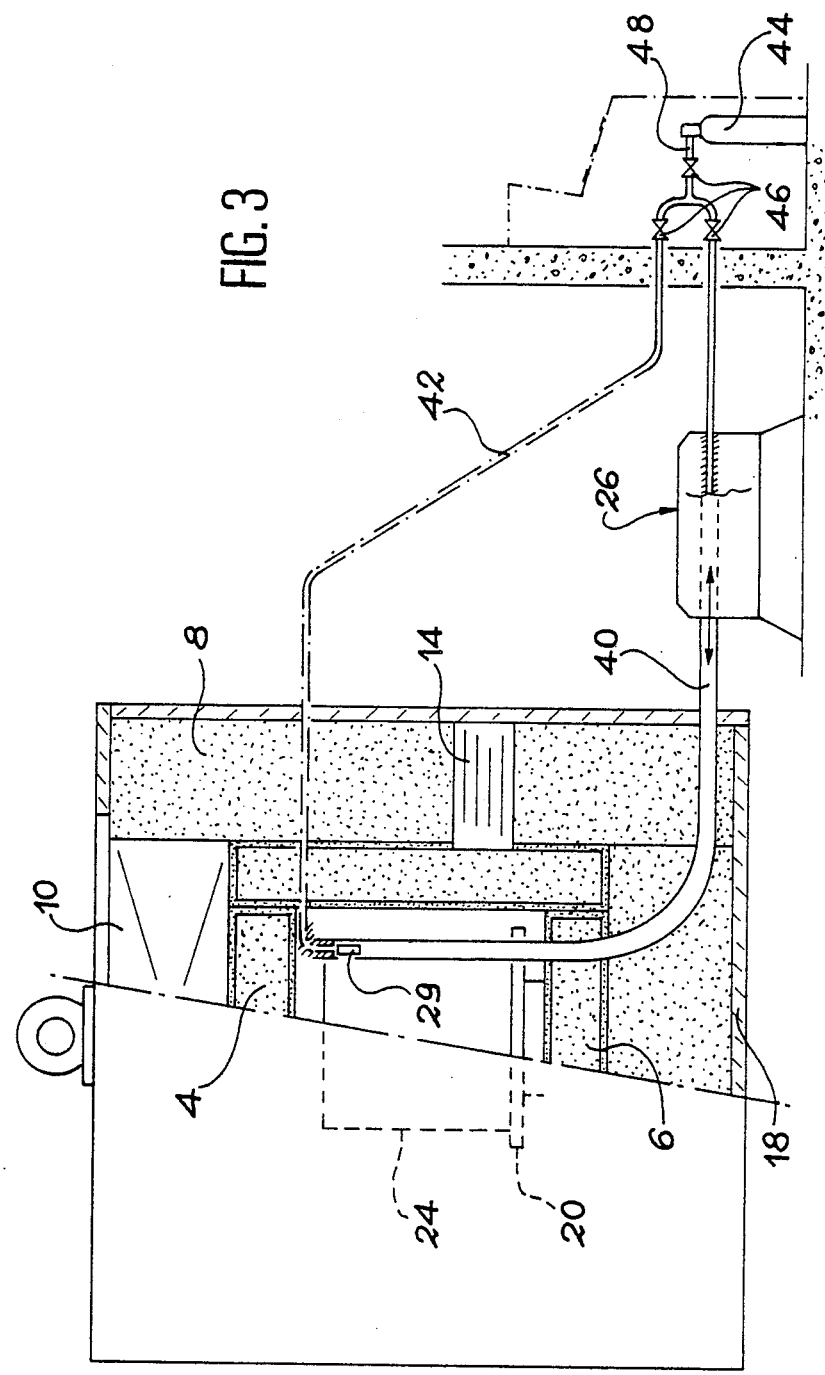

APPARATUS FOR THE CHARACTERIZATION OF FISSILE MATERIAL HAVING AT LEAST ONE NEUTRON RADIATION DETECTOR LOCATED IN A GAMMA RADIATION DETECTION SCINTILLATOR

DESCRIPTION

The present invention relates to an apparatus for characterizing fissile material having at least one neutron radiation detector located within a gamma radiation detection scintillator.

The characterization of fissile material, more particularly contained in radioactive waste emitting alpha radiation is necessary for a number of reasons. It makes it possible to classify the packages of radioactive waste with a view to their storage and whilst satisfying the standards in force concerning activity levels. It permits the classification of these packages on the production site (reprocessing installations) in order to check whether the residual fissile materials are present in quantities below the accepted thresholds. It also permits an evaluation of the nature and quantity of the heavy nuclei contained in the packages in order to evaluate the mass of fissile materials leaving the reprocessing plant.

Radioactive methods permitting a non-intrusive and non-destructive control are suitable for such measurements. A distinction is made between passive and active control methods. The passive methods are based on the detection of neutrons from spontaneous fission processes or interactions between alpha particles and light elements also producing neutrons and/or gamma radiation spontaneously emitted by the radionuclides of the package.

The active methods use an interrogation system making it possible to induce nuclear reactions, which are then analyzed in order to quantitatively and sometimes qualitatively determine the content of radioelements in the nuclear waste. An active detection apparatus consequently comprises a neutron generator or source, a neutron moderator, generally constituted by a hydrocarbon-containing and/or hydrogen-containing material for lowering the energy level of the neutrons in order to increase the probability of producing induced fission processes and a detector for detecting the neutrons and supplying signals corresponding to a system for the measurement and processing of said signals. Most neutron detectors are sensitive to thermal neutrons (e.g. $^3$He proportional detectors), so that neutrons emitted by the spontaneous fission or delayed neutrons, or neutrons resulting from $\alpha$ and n reactions must be slowed down in order to increase the detection probability.

French patent application 85 14 623 of Oct. 2nd 1985 already discloses an apparatus of the active type for fissile material detection. This apparatus comprises a neutron source, panels made from a material able to thermalize the neutrons and a fission neutron detection unit located within the said panels. This apparatus permits the detection of spontaneous neutrons when the neutron source is not functioning and the detection of fission neutrons emitted after a neutron burst from the source. However, it does not permit the detection of spontaneous gamma radiation emitted without any action of the source, as well as delayed gamma radiation.

From NAGRA NTB 82-02, p 88 ff, is also known as a passive and active neutron counting apparatus (Californium Shuffler System), which comprises a $^{252}$Cf source located within a protective casket, an enclosure within which is located a turntable on which is placed the waste unit to be measured and in which the rotation of the table ensures a certain compensation of the heterogeneity of the distribution of the fissile material within the non-nuclear matrix. The apparatus also has a detection system formed from $^3$He proportional counters arranged around the enclosure. A rapid source displacement system makes it possible to pass the latter from its fold back position to its active position within a half second. The counters are connected to an electronic counting system and to a computer for the processing of the signals. However, once again, this apparatus does not make it possible to detect spontaneous and delayed gamma radiation.

However, the detection of delayed gamma radiation makes it possible to determine the total mass of fissile material contained in the matrix. Thus, the average number of delayed gamma radiations emitted by fission is only slightly dependent on the isotope in question. It is therefore representative of the total mass of fissle material. However, the number of delayed neutrons emitted by fission is dependent on the considered isotope. Thus, knowing both the number of delayed neutrons and the delayed gamma number, it is possible to form a ratio between them, which makes it possible to determine the composition of the fissle isotopes in the measured container.

The present invention therefore relates to an apparatus for characterizing fissile material making it possible not only to measure spontaneous and delayed neutrons, but also spontaneous and delayed gamma radiation of the fission induced by means of a neutron radiation source.

The present invention therefore relates to an apparatus for characterizing fissile material having both neutron and gamma radiation detection means, the gamma radiation detection means incorporating a scintillator and at least one photomultiplier associated with said scintillator and the scintillator material also constituting the moderator for thermalizing the fast neutrons directly emitted by the source, as well as the neutrons obtained from the spontaneous fissions of the $\alpha$, n reactions and the neutrons resulting from the fissions induced in the fissile material, the neutron radiation detectors being placed in a scintillator material constituting the moderator.

As a result of this characteristic, a compact apparatus is obtained, whose dimensions can be advantageously reduced by the fact that there is no need to provide a moderator material in addition to the scintillator material and this makes it possible to quantitatively and qualitatively determine the fissile material composition.

Preferably, the enclosure also has a second wall surrounding the wall made from a plastic scintillator material, said second wall being made from a neutron absorbing, thermalizing material, a lead layer also being placed around said second wall.

Other features and advantages of the invention can be gathered from the following description of a non-limitative embodiment and with reference to the attached drawings, wherein show:

FIG. 1: A section in elevation of a fissile material characterization apparatus according to the invention.

Figure 2:
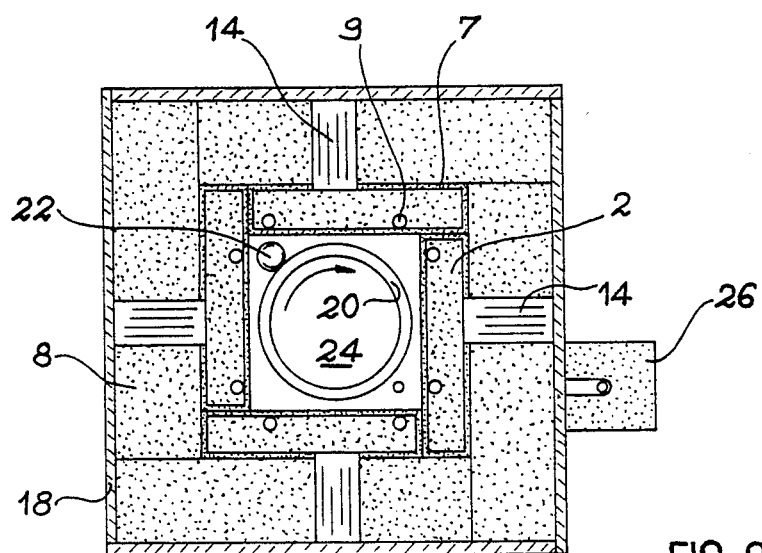

FIG. 2: A cross section of a fissile material characterization apparatus according to the invention.

FIG. 3: A detail illustrating a pneumatic means making it possible to move the source between the foldback protective casket and the interior of the measuring and detection enclosure.

As shown in FIGS. 1 and 2, the fissile material characterization apparatus comprises an entirely sealed enclosure constituted by four vertical walls 2 (cf. in particular FIG. 2), an upper base 4 and a lower base 6. Each of these walls is made from a plastic scintillator material able to produce a scintillation under the effect of gamma radiation. The scintillator material is preferably Altustipe, which is a plexiglass to which anthracene has been added. Each of the walls 2, 4 and 6 is covered with a material 7, which is opaque to light, but transparent to neutrons and gamma radiation, e.g. opaque polyvinyl chloride. This material also has the advantage of being activated only slightly under the effect of gamma radiation and consequently produces little background noise, which would falsify the measurements.

Neutron detectors 9, e.g. constituted by $^3$He tubes are embedded in plates 2. As can be gathered from FIG. 2, there are eight detectors in the represented embodiment. A photomultiplier 14 is associated with each of the scintillator walls 2. In the considered embodiment there are four photomultipliers. The photomultipliers 14 are able to amplify the scintillation occurring in the scintillator plates and produce an electric signal proportional to said scintillation. The photomultipliers 14 and the neutron detectors 9 are connected to a signal processing measuring means 16.

Walls 2, 4 and 6 are also surrounded by a thicker, e.g. 200 mm wall made from a hydrocarbon-containing or hydrogen-containing material, e.g. polyethylene. It is constituted by four walls 8, a plug 10 and a base 12. This second wall participates in the thermalization of the neutrons. It also absorbs parasitic neutrons coming from the outside and which could falsify the measurements. Thus, the inventive apparatus has to be used in the the vicinity of other radiation sources, e.g. radioactive waste, and the radiation from said sources could penetrate the enclosure, which could falsify the measurements. Finally, walls 8, 10, 12 at the same time constitute a biological protection absorbing the neutrons from the source located within the enclosure and which protects operators.

The means is also surrounded by a protective lead layer, e.g. of thickness 20 mm and formed by plates 18 and which has a double function. It firstly protects the external environment against gamma radiation present within the enclosure and on the other hand it prevents the penetration of gamma rays which might come from external sources. Within the enclosure is provided a turntable 20 driven by a motor 22. A basket 24 is placed on the turntable 20 and has a detachable tight casing ensuring that there is no contamination of the enclosure. The package containing the nuclear material to be evaluated is introduced into the enclosure by its upper part by removing the plate 10 forming a plug and then the plate 4. These plates are then refitted in such a way that the enclosure is entirely sealed.

The apparatus also has means making it possible to rapidly introduce a neutron radiation source, e.g. a $^{252}$Cf source 29 into the enclosure. According to a first variant, said means are constituted by a guide tube connected at one of its ends to a foldback casket 26 located outside the enclosure. This casket receives the source 29, when it is not operating and whilst protecting the external environment from the radiation emitted by the source. Guide tube 25 passes through the protective walls of the enclosure, respectively the lead wall 18 and then the polyethylene plates 8, 12 and finally the scintillator material 6. A flexible cable 28 is fixed by one of its ends to a rotary drum 30, whilst the other end of cable 28 is fixed to the source. Drum 30 is rotated by means of a motor, e.g. a stepping motor 32, whose rotation in one direction makes it possible to introduce the source into the enclosure and the rotation in the other direction permits the removal of said source from the enclosure.

According to the constructional variant shown in FIG. 3, the means for introducing source 29 into the enclosure and for removing the same again are of a pneumatic nature. The incorporate a guide tube 40 whose internal section is adequately large to permit the passage of source 29. At one of its ends tube 40 issues into the enclosure and at its other end it is connected to the protective casket 26. In addition, the means have a tube 42 with a smaller section than that of tube 40, so that the source 29 cannot penetrate said tube 42. The ends of tube 42 issue facing the ends of tube 40. Tube 42 is connected to a compressed gas source 44, e.g. a compressed air cylinder. Different valves 46 placed on tube 42 and on tube 48 connecting tube 42 to the compressed gas cylinder 44 permit the pneumatic propelling of source 29 at high speed in order to introduce it into the enclosure or for returning it into the casket 26.

We claim:

1. Apparatus for characterizing fissile material comprising an enclosure for receiving a quantity of fissile material contained in a receptacle, a neutron emitting source (29) for bombarding said fissile material, means (28, 30) for introducing said source (29) into the enclosure and for removing it from said enclosure, neutron radiation detection means (9), moderator means (2, 4, 6) for thermalizing a fission radiation emitted by said fissile material, means (2, 4, 6) being interposed between the neutron radiation detection means (9) and the fissile material, characterized in that it also has gamma radiation detection means (6, 14), which incorporate a scintillator (6) and at least one photomultiplier (14) associated with said scintillator (6), the scintillator material also constituting the moderator for thermalizing the fast neutrons directly emitted by source (29), as well as the neutrons resulting from spontaneous fissions of the $\alpha$, n reactions and the neutrons resulting from fissions introduced in the fissile material, the neutron radiation detectors (9) being embedded in the scintillator material (6) constituting the moderator.

2. Apparatus according to claim 1, characterized in that it has walls made from a plastic scintillator material (6), at least one neutron detector embedded in the plastic scintillator material, a photomultiplier (14) associated with each scintillator and electronic means (16) for processing the signal emitted by the photomultipliers and the neutron detectors.

3. Apparatus according to claim 2, characterized in that the enclosure also has a second wall (8, 10, 12) surrounding the wall made from a plastic scintillator material, said second wall (8, 10, 12) being made from a neutron absorbing, thermalizing material, a lead layer (18) also being placed around said second wall.

4. Apparatus according to claim 3, characterized in that the neutron absorbing material is a hydrocarbon-containing and/or hydrogen-containing material.

5. Apparatus according to any one of the claims 2 to 4, characterized in that the faces of the plastic scintillator material plates (2, 4, 6) are covered with a material (7), which is opaque to light, but transparent to neutrons and gamma radiation and which is only slightly activated under the action of said radiation.

6. Apparatus according to claim 5, characterized in that the material (7) covering the plates is opaque polyvinyl chloride.

7. Apparatus according to any one of the claims 1 to 4, characterized in that the means for introducing the neutron radiation source into the enclosure and for removing said source from the enclosure comprise a drum (30) mounted in rotary manner and rotated by a stepping motor (32), a cable (28) fixed by one end to drum (30) and by the other end to the neutron radiation source (29), as well as a tube (25) connecting the interior of the enclosure to a foldback protective casket (26) located outside said enclosure.

8. Apparatus according to any one of the claims 1 to 4, characterized in that the means for introducing said neutron radiation source into the enclosure and for removing said source from the enclosure comprise a foldback protective casket (26) located outside the enclosure, a guide tube (40) connected by a first end to the protective casket (26) and by a second end to the interior of the enclosure, a pneumatic means for propelling said neutron radiation source within the guide tube, said pneumatic means being constituted by a duct (42) connected on the one hand to the first end of the guide tube (40) and on the other hand to the second end of said guide tube and connected by means of valves (46) to a compressed gas source (44) making it possible to connect the first or second end of the guide tube to said compressed gas source (44).

* * * * *